United States Patent [19]

Gueret

[11] Patent Number: 5,393,809
[45] Date of Patent: Feb. 28, 1995

[54] POLYMERIC SYNTHETIC MATERIAL WHICH HAS AN ANTISEPTIC AND/OR ANTIOXIDANT ACTION AND PROCESS FOR THE MANUFACTURE OF THE SAID MATERIAL

[75] Inventor: Jean-Louis H. Gueret, Paris, France

[73] Assignee: L'Oreal, Paris, France

[21] Appl. No.: 93,753

[22] Filed: Jul. 20, 1993

[30] Foreign Application Priority Data

Jul. 21, 1992 [FR] France .................. 92 08975

[51] Int. Cl.⁶ ............... C08K 3/10; C08L 1/02
[52] U.S. Cl. .................... 524/35; 524/27; 524/47; 523/210
[58] Field of Search ............ 523/210; 524/35, 47, 524/27

[56] References Cited

U.S. PATENT DOCUMENTS

| | | | |
|---|---|---|---|
| 3,138,565 | 6/1964 | Rosenberger | 524/35 |
| 3,484,396 | 12/1969 | Gelhaar | 524/35 |
| 3,501,419 | 3/1970 | Bridgeford | 524/35 |
| 3,516,953 | 6/1970 | Wood | 524/35 |
| 3,907,726 | 9/1975 | Tomiyama | 524/35 |
| 3,929,696 | 12/1975 | Nistri et al. | 524/35 |

FOREIGN PATENT DOCUMENTS

| | | |
|---|---|---|
| 0116865 | 8/1984 | European Pat. Off. . |
| 0444939 | 9/1991 | European Pat. Off. . |
| 0580460 | 1/1993 | European Pat. Off. . |
| 2322801 | 4/1977 | France . |
| 401468 | 5/1966 | Switzerland . |

OTHER PUBLICATIONS

French Search Report–FR 92 08975.

Primary Examiner—Kriellion S. Morgan
Attorney, Agent, or Firm—Cushman Darby & Cushman

[57] ABSTRACT

Synthetic material containing at least one heat-cured polymer and an impregnated filler which has, on contact, an antiseptic and/or antioxidant action on a fluid product, in which the filler is an organic filler impregnated with at least one water-soluble antiseptic agent and/or with at least one water-soluble antioxidant agent.

The antiseptic and/or antioxidant agents are capable of being released when the synthetic material is in contact with a fluid product and of at least partially preventing the degradation of the fluid product by microorganisms or by oxygen.

23 Claims, No Drawings

POLYMERIC SYNTHETIC MATERIAL WHICH HAS AN ANTISEPTIC AND/OR ANTIOXIDANT ACTION AND PROCESS FOR THE MANUFACTURE OF THE SAID MATERIAL

The present invention relates to a polymeric synthetic material which has an antiseptic and/or antioxidant action, which can be employed, in particular, for manufacturing by moulding articles capable of releasing antiseptic and/or antioxidant agents and, consequently, preventing degradation, by microorganisms such as viruses, bacteria, moulds or fungi, and/or by atmospheric oxygen, of fluid products with which the said articles are in contact.

Such materials are found to be useful in many fields. The problem to be solved, according to the present invention, was to find a polymer that makes it possible to manufacture by moulding the components of a dispensing device for fluid product. It is known that in devices for dispensing fluid products, especially cosmetics, in successive doses, a fraction of the dispensed product remains in the dispensing channel when the dispensing has ceased. The product remaining in the dispensing channel is in contact with air and is liable to be degraded under the effect of microorganisms in the atmosphere and/or of atmospheric oxygen. As a result, the next dispensed dose may contain harmful products and may, for example, cause irritation when applied to the skin. An attempt is therefore made to avoid this degradation.

It is known to prepare polymers containing metal ions which impart an antiseptic action to the polymers. It is also known to prepare polymers containing an inorganic filler into which metal ions are introduced by impregnation with the aid of water-soluble salts. According to EP-A-0,116,865 zeolites are impregnated with metal ions; however, the combined action of the zeolites and of the metal ions tends to cause crosslinking and very rapid hardening of the polymers. It is therefore necessary to mould the zeolite-filled polymer and subsequently to impregnate only the zeolites situated at the surface of the moulded article with the aid of a solution containing metal ions. Under these conditions the proportion of impregnated zeolites is low and, as a result, the antiseptic activity of the polymer is too weak to solve the problem set out above.

In EP-A-0,444,939 it is proposed to mix a polymer with silica particles coated with a metal aluminosilicate which has an antiseptic activity. This process avoids having to impregnate a silica gel and makes it possible to obtain particles which have a high content of metal ions; but it is complicated and costly.

According to the present invention it has been found that it is possible to obtain a polymer containing a filler preimpregnated with active agent without causing the crosslinking and the hardening of the filled polymer too rapidly, provided that the polymer is a heat-curable resin and that the filler is an organic filler impregnated with antiseptic and/or antioxidant agent.

It has furthermore been found that, when at least a proportion of the surfaces of the dispensing channel of a device for dispensing fluid product is made of a heat-cured polymer according to the invention containing an organic filler preimpregnated with at least one antiseptic agent and/or at least one antioxidant agent, the degradation of the product remaining in this dispensing channel can be avoided completely, provided that the dispensing device comprises a closure system without air uptake and that, even in the absence of a closure system without air uptake, the degradation of the dispensed product can be greatly decreased.

French Patent Application No. 92-08,976 filed by the Applicant Company on Jul. 21, 1992 describes the use of the polymeric synthetic material of the present application in a dispensing head comprising a closure system without air uptake.

The subject of the present invention is therefore a synthetic material containing at least one heat-cured polymer and an impregnated filler, the said material having, on contact, an antiseptic and/or antioxidant action on a fluid product, characterized in that the filler is an organic filler impregnated with at least one water-soluble antiseptic agent and/or with at least one water-soluble antioxidant agent.

The heat-cured polymer is preferably prepared from an aminoplastic resin. The aminoplastic resin may be a melamine-formaldehyde resin but is preferably a urea-formaldehyde resin.

The antiseptic agent is preferably a water-soluble metal salt and, more particularly, a water-soluble copper, zinc or silver salt, preferably a copper or zinc sulphate or silver nitrate. Copper sulphate is preferred.

The antioxidant agent is preferably chosen from the group consisting of gentisic, homogentisic, pidolic, ascorbic and citric acids and mixtures thereof.

According to the invention the antiseptic and/or antioxidant agents are in a form impregnated onto an organic filler in the particulate state. The filler is advantageously in the form of powder or of small-sized granules; it may also be in the form of fibres. In the case of powder or granules the filler preferably has a particle size of between 5 $\mu$m and 2 mm. In the case of fibres, the latter preferably have a length of between 0.1 and 2 mm and a diameter of between 5 $\mu$m and 0.5 mm.

The organic filler advantageously consists of at least one natural product based on polysaccharide(s). In particular, the organic filler may be wood powder or sawdust, cellulose, more particularly cotton, starch, carragenate gum, alginates, xanthans, scleroglucans or mixtures thereof. More particularly, the filler consists of cellulose.

The material according to the invention preferably contains 30 to 98% by weight of heat-curable resin and 2 to 70% by weight of impregnated organic filler(s). It preferably contains from 50% to 70% by weight of impregnated organic filler(s).

From 0.01 to 50% by weight of antiseptic and/or antioxidant agent(s) are preferably bound by impregnation onto the filler, the total quantity of bound agent(s) being preferably between 2 and 20% by weight (the percentages being taken in relation to the weight of the filler).

A further subject of the present invention is the preparation of a polymeric synthetic material as defined above, characterized in that at least one aminoplastic heat-curable resin is mixed with at least one organic filler in the particulate state, the said filler being impregnated with at least one antiseptic agent and/or at least one antioxidant agent, and in that the mixture is at least partially crosslinked.

According to the present invention the filler may be impregnated by being immersed in an aqueous solution which advantageously has a concentration of antiseptic and/or antioxidant agent(s) close to saturation, and by then being dried, especially for 24 hours at ambient temperature.

The filler may be impregnated either before being mixed with the heat-curable resin or after its mixing with the heat-curable resin, the filler being then impregnated before the crosslinking of the heat-curable resin. It should be noted that the organic filler present in the polymer can no longer be impregnated after crosslinking of the polymer. When the filler has been mixed with the heat-curable resin, the material obtained must be in particulate form to be capable of being subsequently employed. The polymeric synthetic material according to the invention can be employed in the form of granules or of beads which are placed in contact with the product to be treated; the granules or the beads are crosslinked by any known process for crosslinking heat-curable resins. However, it is preferably moulded, it being possible for the moulding to be performed by any known process for heat-curable resins.

Depending on the conditions of the moulding process chosen, it is possible to obtain articles made of heat-curable resin exhibiting controlled release characteristics. For example, the moulding may be performed in a compression mould, with simultaneous heating, for example at 130° to 150° C. for 3 to 4 minutes, optionally in the presence of a catalyst; this produces a relatively dense article exhibiting a low ability to release the antiseptic agent and/or antioxidant agent. If it is desired to increase the rate of release, a slight abrasion may be produced on at least a proportion of the surface of the moulded article which is to be in contact with the fluid product to be dispensed. Another method for increasing the rate of release of antiseptic agent and/or of antioxidant agent consists in introducing the impregnated resin into a mould and in compacting cold; next, without applying compression, heating is applied, for example, for 5 or 10 minutes at 130° to 150° C.; a lightweight article is obtained, resembling a sintered article and exhibiting a high release capacity.

As indicated above, the mixture of heat-curable resin and of impregnated filler(s) can be moulded. In fact, it has been found that the heat-curable resin does not crosslink immediately in the presence of impregnated organic filler(s). For example, in the presence of an organic filler impregnated with copper, zinc or silver salts, it is necessary to wait 8 months at ambient temperature for 70% by weight of the heat-curable resin to be crosslinked and for the material to no longer be able to be employed for moulding; it can, however, still be employed as it is, in the form of granules or beads.

The example given below by way of illustration and without any limitation being implied will enable the invention to be better understood.

A urea-formaldehyde powder product sold by the "Perstrop" company is taken, the said product containing 30% by weight of urea-formaldehyde resin and 70% by weight of cellulose as filler. The said product is immersed at ambient temperature in a saturated aqueous solution of zinc and copper sulphate (50:50), as antiseptic agent, and of citric acid, as antioxidant agent, for approximately 10 min, while being vigorously stirred so that the filler absorbs the aqueous solution and becomes impregnated with copper sulphate, zinc sulphate and citric acid. The powder is next separated from the solution and is dried in a stream of dry air at ambient temperature for 24 hours. When the powder is dehydrated, it contains 8% by weight of copper sulphate, of zinc sulphate and of citric acid.

Less than 8 days after its preparation, the powder thus obtained is introduced into a cold mould, is compacted and is heated to a temperature of 135° C. for 3 min without compression being applied. The moulded article obtained can be employed as an article defining the dispensing channel in a dispensing head for cosmetic cream; this cream is packaged in a leakproof container and the dispensing head does not comprise any system isolating the dispensing channel from the outside. It has been found that, after a first dispensing, the cream which has remained in the dispensing channel for a week has not undergone any degradation, either by any microorganism or by atmospheric oxygen.

I claim:

1. A synthetic polymeric material comprising a mixture of a heat-cured urea-formaldehyde resin and a particulate organic filler selected from the group consisting of wood powder, wood sawdust, cellulose, starch, carragenate gum, an alginate, a xanthan, a scleroglucan and mixtures thereof, said particulate organic filler being impregnated with an antiseptic agent selected from the group consisting of a water-soluble copper salt, a water-soluble zinc salt and a water-soluble silver salt.

2. The synthetic polymeric material of claim 1 wherein said water-soluble copper salt is copper sulphate or copper nitrate.

3. The synthetic polymeric material of claim 1 wherein said water-soluble zinc salt is zinc sulphate or zinc nitrate.

4. The synthetic polymeric material of claim 1 wherein said water-soluble silver salt is silver sulphate or silver nitrate.

5. The synthetic polymeric material of claim 1 wherein said particulate organic filler is cellulose.

6. The synthetic polymeric material of claim 1 wherein said heat-cured urea-formaldehyde resin is present in an amount ranging from 30 to 98 weight percent and said particulate organic filler impregnated with said antiseptic agent is present in an amount ranging from 2 to 70 weight percent.

7. The synthetic polymeric material of claim 6 wherein said particulate organic filler impregnated with said antiseptic agent is present in an amount ranging from 50 to 70 weight percent.

8. The synthetic polymeric material of claim 1 wherein said particulate organic filler contains from 0.01 to 50 percent by weight of said antiseptic agent.

9. The synthetic polymeric material of claim 1 wherein said particulate organic filler comprises powders or granules having a mean dimension ranging from 5 $\mu$m to 2 mm.

10. The synthetic-polymeric material of claim 1 wherein said particulate organic filler comprises fibers having a length ranging from 0.1 to 2 mm and a diameter ranging from 5 $\mu$m and 0.5 mm.

11. A process for preparing the synthetic polymeric material of claim 1 comprising mixing said heat-cured urea-formaldehyde resin with said particulate organic filler impregnated with said antiseptic agent and partially crosslinking the resulting mixture.

12. The process of claim 11 which includes impregnating said particulate organic filler with said antiseptic agent prior to mixing said heat-cured urea-formaldehyde resin with said particulate filler.

13. The process of claim 11 which includes impregnating said particulate organic filler with said antiseptic agent subsequent to mixing said heat-cured urea-formaldehyde resin with said particulate filler.

14. The process of claim 11 wherein impregnating said particulate organic filler comprises immersing said organic filler in an aqueous solution of a water-soluble salt of said antiseptic agent and drying the resulting impregnated particulate organic filler.

15. The process of claim 11 wherein said resulting mixture is heat-cured in a mold under compression by elevating the temperature to a degree sufficient to produce a molded article.

16. The process of claim 15 which includes slightly abrading said molded article on at least a proportion of the surface thereof.

17. The process of claim 11 which includes filling a mold with said resulting mixture in the cold state, applying compression to said mixture in the cold state and elevating the temperature of said mixture so as to cure said mixture.

18. A container for dispensing a fluid product degradable by microorganisms or atmospheric oxygen, said container provided with a dispensing head having a dispensing channel through which said fluid product is dispensed, said dispensing channel comprising a polymeric material comprising a mixture of heat-cured urea-formaldehyde resin and a particulate organic filler selected from the group consisting of wood powder, wood sawdust, cellulose, starch, carragenate gum, an alginate, a xanthan, a scleroglucan and mixtures thereof, said particulate organic filler being impregnated with a water-soluble antiseptic agent, a water-soluble antioxidant agent and a mixture thereof.

19. The container of claim 18 wherein said water-soluble antiseptic agent is selected from the group consisting of a water-soluble copper salt, a water-soluble zinc salt and a water-soluble silver salt.

20. The container of claim 18 wherein said water-soluble antioxidant agent is selected from the group consisting of gentisic acid, homogentisic acid, pidolic acid, ascorbic acid, citric acid and mixtures thereof.

21. The container of claim 18 wherein said particulate organic filler is cellulose.

22. The container of claim 18 wherein said heat-cured urea-formaldehyde resin is present in said synthetic polymeric material in an amount ranging from 30 to 98 weight percent and said particulate organic filler impregnated with said antiseptic agent or antioxidant agent or a mixture thereof is present in an amount ranging from 2 to 70 weight percent of said synthetic polymeric material.

23. A dispensing channel in a dispensing head of a container for dispensing through said dispensing channel a fluid product degradable by microorganisms or atmospheric oxygen, said dispensing channel comprising a polymeric material comprising a mixture of heat-cured urea-formaldehyde resin and a particulate organic filler selected from the group consisting of wood powder, wood sawdust, cellulose, starch, carragenate gum, an alginate, a xanthan, a scleroglucan and mixtures thereof, said particulate organic filler being impregnated with a water-soluble antiseptic agent or a water-soluble antioxidant agent or a mixture thereof.

* * * * *